Figure 1:
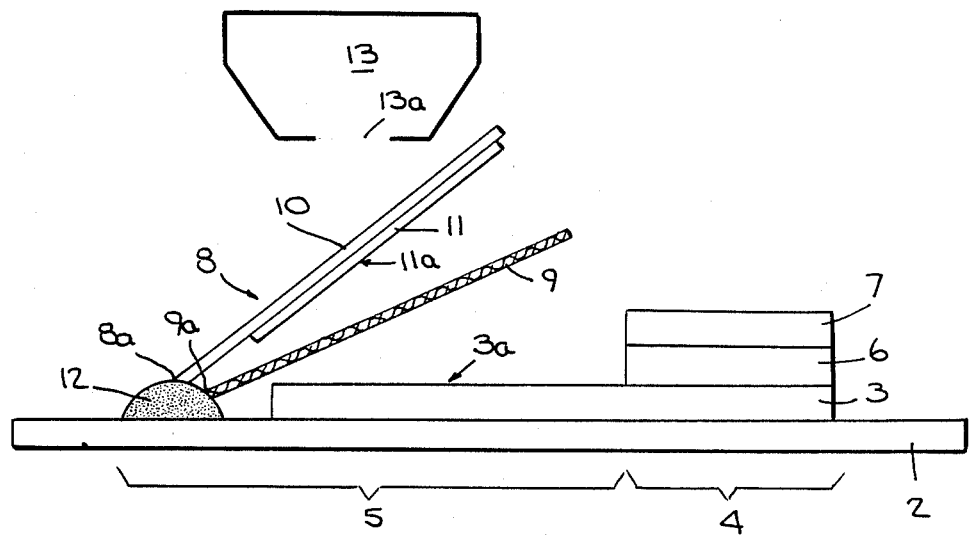

United States Patent [19]

Deneke et al.

[11] Patent Number: 4,876,067
[45] Date of Patent: Oct. 24, 1989

[54] MULTILAYER TEST STRIP DEVICE WITH A DISSOLVABLE REAGENT LAYER

[75] Inventors: Ulfert Deneke, Rimbach-Zotzenbach; Rolf Nagel, Bürstadt; Anselm Rothe, Birkenau; Helmut Freitag, Weinheim, all of Fed. Rep. of Germany

[73] Assignee: Boehringer Mannheim GmbH, Mannheim, Fed. Rep. of Germany

[21] Appl. No.: 89,352

[22] Filed: Aug. 25, 1987

[30] Foreign Application Priority Data

Sep. 12, 1986 [DE] Fed. Rep. of Germany ....... 3630999

[51] Int. Cl.⁴ .......................................... G01N 21/77
[52] U.S. Cl. ....................................... 422/56; 422/57; 422/58; 436/169; 435/805
[58] Field of Search ................. 422/56, 73, 57, 58; 436/169; 435/805

[56] References Cited

U.S. PATENT DOCUMENTS

| | | | |
|---|---|---|---|
| 3,785,930 | 11/1974 | Ellis | 422/56 |
| 3,917,453 | 11/1975 | Milligan et al. | 422/56 |
| 3,933,594 | 1/1976 | Milligan et al. | 435/15 |
| 3,936,357 | 2/1976 | Milligan et al. | 435/15 |
| 4,061,468 | 12/1977 | Lange et al. | 422/56 |
| 4,108,729 | 8/1978 | Mennen | 422/56 |
| 4,110,079 | 8/1978 | Schaeffer et al. | 422/56 |
| 4,223,089 | 9/1980 | Rothe et al. | 422/56 |
| 4,229,813 | 10/1980 | Lilly et al. | 422/56 |
| 4,275,031 | 6/1981 | Fischer et al. | 422/57 |
| 4,387,164 | 6/1983 | Hevey et al. | 422/72 |
| 4,390,343 | 6/1983 | Walter | 422/56 |
| 4,477,575 | 10/1984 | Vogel et al. | 422/57 |
| 4,486,537 | 12/1984 | Koyama et al. | 422/57 |
| 4,523,853 | 6/1985 | Rosenbladt et al. | 356/448 |
| 4,647,541 | 3/1987 | Guadagno et al. | 422/56 |
| 4,673,654 | 6/1987 | Talmage | 422/56 |
| 4,693,751 | 9/1987 | Den Boer et al. | 106/209 |
| 4,717,656 | 1/1988 | Swanljung | 422/58 |
| 4,780,280 | 10/1988 | Berger et al. | 422/58 |
| 4,804,518 | 2/1989 | Levine et al. | 422/58 |

FOREIGN PATENT DOCUMENTS

| | | | |
|---|---|---|---|
| 239002A | 9/1987 | European Pat. Off. | 422/57 |
| 3130749 | 2/1963 | Fed. Rep. of Germany | 422/58 |

*Primary Examiner*—Barry S. Richman
*Assistant Examiner*—Lyle Alfandary-Alexander
*Attorney, Agent, or Firm*—Felfe & Lynch

[57] ABSTRACT

The present invention provides a multi-layer test carrier (1) for the analytical determination of a component in a liquid sample, especially in a body fluid, having a first carrier layer (2) and a second carrier layer (10), at least one of which is transparent, a liquid-absorbing layer (3) being applied to the first carrier layer (2) and a reagent layer (11) containing at least one reagent being applied to the second carrier layer (10), the carrier layers being so arranged and fixed that the surfaces (3a, 11a) of the absorbing layer and of the reagent layer facing away from the carrier layer can be brought into contact with one another and can be pressed against one another, wherein the reagent layer (11) is soluble substantially without residue in the sample liquid and the take-up ability of the liquid-absorbing layer (3) for the sample liquid is so great that an amount of liquid absorbed therein suffices in order to dissolve the reagent layer free of residues so that substances contained in the reagent layer (11) pass over from the reagent layer (11) into the liquid-absorbing layer (3) when the two layers are pressed against one another.

19 Claims, 1 Drawing Sheet

MULTILAYER TEST STRIP DEVICE WITH A DISSOLVABLE REAGENT LAYER

The present invention is concerned with a multi-layer test carrier.

More particularly, the present invention is concerned with a multi-layer test carrier for the analytical determination of a component in a liquid sample, especially in a body fluid, with a first carrier layer and a second carrier layer, at least one of which is transparent, an absorbing layer being applied to the first carrier layer and a reagent layer containing at least one reagent being applied to the second carrier layer, the carrier layers being so arranged and fixed that the surfaces of the absorbing layer and of the reagent layer facing away from the carrier layer can be brought into contact with one another and can be pressed against one another.

Test carriers have achieved considerable importance in the analysis of liquids. Especially in clinical chemistry, which includes the qualitative and quantitative determination of components in body fluids, especially in blood and urine, the advantages thereof are greatly appreciated. Whereas the well-known methods using liquid reagents require the use of a number of steps, analytical determinations with the help of test carriers are characterized by an extremely simple handling. In the case of the analysis of urine, test carriers in the form of test strips are generally used which are briefly dipped into the sample and thereafter evaluated either visually or with the use of appropriate apparatus. In the case of blood analyses, a drop of serum or, in the case of an especially advanced type of test carrier, a drop of blood is applied to a particular place on the test carrier.

The reaction of the liquid with the reagents present on the test carrier leads to a detectable change of the test carrier and usually to a change of the colour thereof, for example by the formation or liberation of a coloured material. However, the reaction can also lead to the formation or change of a fluorescing substance or a substance which can be detected optically or in some other way. Test carriers for the determination of blood components are preponderantly evaluated with the help of appropriate apparatus. The present invention is especially concerned with a test carrier for the quantitative determination of components of a liquid with the help of a reflection photometer or of some other apparatus for optical evaluation.

Test carriers are produced in various embodiments. At the start of the development thereof, test strips were almost exclusively used which carried one or more test zones. Initially, the test zones consisted preponderantly of paper or of a similar porous material which was capable of absorbing due to the capillary forces between the individual fibres. Subsequently, test zones were increasingly made in the form of polymeric layers in which reagents are embedded in a matrix which can also be called a film layer. Such reagent films can, in principle, be divided into two different types, on the one hand, porous layers which, on the basis of capillary forces, take up the sample liquid and, on the other hand, swellable films into which the sample liquid, which, in the case of body fluids, is always of an aqueous nature, can penetrate slowly due to the take up of the water into the structure of the film. It is a common feature of both types that the reagents are embedded in the film and, during course of the reaction, remain therein, i.e. the sample penetrates into the film in which the reaction with the reagents takes place.

In the meantime, greatly differing types of test carriers have also been developed with regard to the external structure. Thus, for example, quadratic platelets are used which, like a photographic slide, contain, in a cardboard frame, a test zone with the reaction film which is also quadratic. Some manufacturers prefer the well-known test strips of similar construction.

Federal Republic of Germany Patent Specification No. 31 30 749 describes a test carrier of the initially mentioned type. In this case, the first carrier layer is formed by a longitudinal base film as in the case of a test strip, the absorbing layer being arranged thereon. On to the base film is fixed one edge of a rectangular covering film which is as wide as the base film but considerably shorter than this. The fixing point is near the end of the absorbing layer. On the side of the covering film facing the base film is provided a reagent layer which is preferably in the form of a reagent film. The covering film with the reagent film forms a flap, the connection with the base film being such that, in a stationary state, the flap does not touch the absorbing layer. It is thereby possible to divide up the chronological course of a reaction into two stages. The sample is first applied to the absorbing layer, whereby it can react with reagents which are possibly incorporated into this layer. At a particular point of time, the covering film with the reagent layer is pressed on to the base film. Due to this full-faced contact, the sample contained in the absorbing layer can pass over into the reagent layer on the flap. A further reaction there takes place which results in a detectable signal, for example a colour change.

With the help of the multi-layer test carriers which are today obtainable, even laborious determinations can be carried out. Since the various reagents which are necessary for this purpose must frequently be applied to different layers which are separated from one another, such test carriers frequently have a comparatively large number of layers, all of which must be moistened through with the applied sample. Since, on the one hand, the amount of sample with which the test is to be carried out is to be kept as small as possible (about 30 to 50 $\mu$l.), the individual layers are made as thin as possible. For this purpose, the above-mentioned film layers are especially suitable which, in comparison with layers based on paper, are also characterised by an especially good homogeneity. However, the use of very thin layers also gives rise to new problems, inter alia because there is a danger that reagents, when they are dissolved by the sample liquid, will migrate from one layer and penetrate into another layer. If, for example, a colour is formed in a reagent layer due to a reaction between a component of the sample or a product of a preceding reaction, then it is important that the coloured substance thus formed remains in the layer in which it is to be measured.

Starting from this problem, there is a need for test carriers which only require a small amount of sample but which permit a multi-layer construction and which avoid the problem of an uncontrolled diffusion of reagent components from one layer into an adjacent layer.

This need is solved in the case of a test carrier of the initially described type in that the reagent layer is soluble in the sample liquid substantially free of residues and the take-up capacity of the absorbing layer for the sample liquid is so great that the amount of liquid absorbed therein suffices to dissolve the reagent layer without residue so that substances contained in the reagent layer pass from the reagent layer into the liquid-absorbing layer when the two layers are pressed together.

In the case of the test carrier according to the present invention, the course of the test thus differs, in principle, from that of Federal Republic of Germany Patent Specification No. 31 30 749 in that the reaction between the reagents of the reagent layer and the sample does not take place in the reagent layer but in the absorbing layer.

It is important that the reagent layer dissolves in the sample layer quickly and substantially free of residues. Consequently, it preferably does not contain any pigments. "Substantially free of residue" is thereby to be understood in relation to the desired exactitude of the measurement. If undissolved parts of the reagent layer remain behind on the second carrier layer, this results in a falsification of the measurement result. Therefore, the dissolving must be so complete that the desired exactitude of the measurement is achieved.

Furthermore, the volume of liquid which can be kept in the liquid-absorbing layer is of importance. It is determined by the thickness of the layer and its absorption ability for the liquid.

The reagents contained in the reagent layer are to penetrate completely into the absorbing layer. In order to simplify this, the reagent layer should be thinner than the liquid-absorbing layer and is preferably at most half as thick as this.

Important for the success of the present invention is the choice of an appropriate material from which the reagent layer is made. According to a preferred embodiment, the reagent layer is made as a film of a high molecular weight, polymeric material. The material is soluble in water as well as the film made of it. This property is called "reversible solubility". Materials which are especially preferred as film formers are those which are also used as binding or swelling agents or as thickening agents. By way of example, there are mentioned polyvinylpyrrolidone, polyvinyl alcohol, methyl cellulose, methylhydroxyethyl cellulose, hydroxyethyl cellulose and alginates, especially sodium alginate.

Xanthan has proved to be an especially preferred film former. This is a natural, high molecular weight polysaccharide which is commercially available from the Kelco Division of Merck & Co., USA, under the trade names "Keltrol" and "Kelzan". It can be produced with the help of the micro-organism *Xanthomonas campestris*. The cell wall of this micro-organism is externally encompassed by xanthan. The material is obtained by appropriate purification methods from cultures of the mentioned micro-organism. The structure contains three different monosaccharides, namely, mannose, glucose and glucuronic acid. More detailed information is available especially from publications of the above manufacturer.

The liquid-absorbing layer can consist of a large number of materials which fulfil the above-mentioned requirements with regard to their ability to take up sample fluids. Papers, fleece and such film layers which, on the basis of an open structure containing numerous capillary gaps, have a considerable ability to take up liquids, have proved to be especially suitable.

As mentioned above, the reaction between the sample fluid contained in the absorbing layer, which has possibly already undergone previous preliminary reactions, with the reagents of the reagent layer leads to a detectable signal and especially to a colour formation. Other possibilities for detectable signals have already been mentioned. In the following, however, by way of example and without limitation of the generality, reference is only made to the formation of a colour and to the corresponding photometric measurement with the help of a reflection photometer.

In the case of the test carrier according to the present invention, as mentioned, the reagents pass over into the liquid-absorbing layer so that there, and not in the reagent layer itself, the colour formation takes place. Surprisingly, we have found that, due to the fact that the liquid-absorbing layer is comparatively thick and is preferably made of a fibrous material, the quality of the optical measurement is not impaired. There is even obtained an especially good measurement exactitude when the liquid-absorbing layer is made from a material with a comparatively low optical absorption ability so that it is penetrated by the measurement light of an appropriate remission photometer. In this case, at least one of the carrier layers and preferably the base film must have diffuse reflecting properties. In this way, the measurement light is reflected back through the liquid-absorbing layer and is detected by the measurement receiver of the deflection photometer. Since the measurement light passes twice through the complete layer thickness of the liquid-absorbing layer, the optical layer thickness forming the basis of the measurement is comparatively large which results in an excellent sensitivity of the measurement. In contradistinction thereto, in the case of the test carriers previously known from Federal Republic of Germany Patent Specification No. 31 30 749, the reagent layers preferably contain a high proportion of pigments in order that substantially only the colour formation near the surface of the reagent layer facing the covering film is observed. This was necessary in order to avoid measurement errors due to the diffusing away of coloured materials but resulted in too low an optical layer thickness and thus in a loss of sensitivity.

Figure 2:
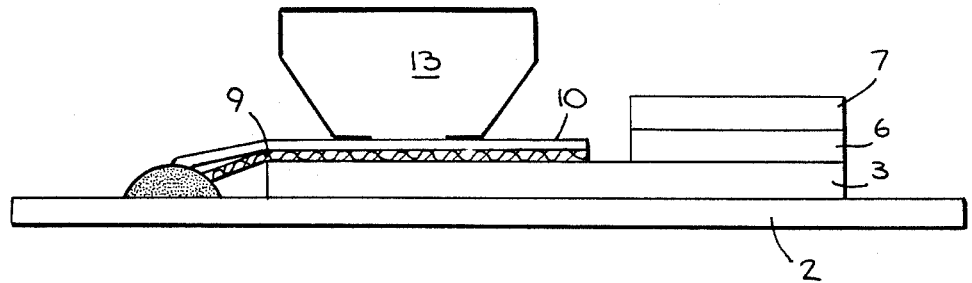

The present invention will now be explained in more detail, with reference to the accompanying drawings, in which:

FIG. 1 is a longitudinal section through a test carrier according to the present invention in which the reagent layer is not pressed on to the liquid-absorbing layer; and FIG. 2 is a test carrier according to FIG. 1 in which the reagent layer is pressed against the liquid-absorbing layer.

The test carrier 1 illustrated in FIG. 1 comprises a base film 2 which serves as a carrying layer for an absorbing layer 3 which lies full-facedly thereon. The base film 2 is narrow and extends longitudinally as in the case of a test strip. The layer arranged thereon have the same width as the base film 2 but extend only over a part of its length.

The total test area of the test carrier 1 can be subdivided into a sample application zone 4 and into an evaluation zone 5. In the sample application zone 4, above the absorbing layer 3 is provided a pre-reagent layer 6 and a plasma separation layer 7. These two layers only cover a part of the absorbing layer 3.

In the evaluation zone, the test carrier has a flap, the whole of which is indicated by 8, and a reagent carrier 9. The flap 8 and the reagent carrier 9 are both rectangular and have the same breadth as the carrier layer 2. With one of their short edges 8a and 9a, respectively, they are fixed to the base film 2 in such a way that, in an untensioned state, they are not in contact with the absorbing layer 3 but can be brought into contact with the layer 3 by external pressure.

The flap 8 comprises a covering film 10 and a reagent layer 11 coated thereon. In the Figure, the reagent layer 11 only covers a part of the length of the covering film 10. However, for production reasons, it can be preferable to coat the whole of the covering foil 10 with a reagent layer 11 on the surface facing the absorbing layer 3.

The reagent carrier 9 has an open composite structure for liquid so that it does not hinder the liquid exchange between the reagent layer 11 and the absorbing layer 3. It preferably consists of a carrier matrix of open, very thin tissue or paper on which are impregnated the soluble reagents. The carrier matrix must, on the one hand, be firm enough in order not to be damaged in a dry state during storage and handling of the test carrier. On the other hand, it must be so thin and open in its structure that the optical measurement is not disturbed to an extent which impairs the measurement exactitude. For this purpose, tea bag power as for example a long fibrous, absorptive paper of a thickness of about 50 $\mu$m and a weight per area of about 12 g/m$^2$ has proved to be especially suitable.

For carrying out an analysis, a droplet of, for example, 30 $\mu$l. of blood is applied to the plasma separation layer 7. It percolates through this layer, the erythrocytes in the blood thereby being separated (for more details, see U.S. Pat. No. 4,477,575). The plasma thus obtained passes into the pre-reagent layer 6 where it dissolves one or more of the reagents contained therein which can react with the sample. The sample passes from the pre-reagent layer 6 into the absorbing layer 3 and is transported by this in the longitudinal direction of the test carrier into the evaluation zone 5. For this purpose, the absorbing layer 3 has capillary transport properties in this direction, i.e. in the direction of its planar elongation.

The absorbing layer 3 and the plasma separation layer 7 are preferably made of glass fibres (cf. U.S. Pat. No. 4,477,575). However, they can also be made of another material which fulfils the above-mentioned conditions.

In the evaluation zone 5, in the above-described operational state, the plasma is available in the absorbing layer 3, a pre-reaction with the pre-reagent of layer 6 possibly already having taken place. At a precisely defined time, a further reaction can be initiated by pressing down the flap 8 on to the absorbing layer 3. FIG. 2 shows the state in which the absorbing layer 3 and the reagent layer 11 are in contact with one another with their facing surfaces 3a and 11a, respectively, in a manner enabling a liquid exchange to take place.

In the case of the embodiment illustrated in the Figures, the pressure is exerted on the flap 8 by the measurement system 13 of an appropriate evaluation apparatus. At the mentioned definite point of time at which the flap 8 is to be pressed upon, the measurement system 13 moves obliquely downwardly from the position shown in FIG. 1 until it lies upon the covering film 10 and the flap 8 is pressed against the absorbing layer 3. Further details of an appropriate construction of an optical measurement system are given in U.S. Pat. No. 4,523,853. An appropriate construction for holding the test carrier and for pressing down the flap is given in European Patent Specification No. 0,129,220.

After pressing the reagent layer 11 on to the absorbing layer 3, the sample liquid dissolves the reagent layer 11 and the reagents contained therein pass into the absorbing layer 3. The reagents impregnated on the reagent carrier 9 are dissolved therefrom and also pass into the absorbing layer 3. A reaction thereupon takes place therein which leads to a coloration characteristic for the desired analytical determination which can be detected reflection-photometrically with the measurement system 13.

For this purpose, measurement light is shone through the window 13a of the measurement system 13 and the covering film 10 of the flap 8, as well as through the reagent carrier 9 into the absorbing layer 3. If the absorbing layer 3 is highly pigmented, the measurement light, after more or less deep penetration into the absorbing layer 3, will be diffusely reflected back and detected in known manner by the measurement system 13. However, especially preferably, the optical absorption ability of the absorbing layer 3 is comparatively small so that the measurement light penetrates through the whole of the thickness of the layer and is first diffusely reflected back by the base film 2 which, in this case, is highly pigmented. In this way, the whole layer thickness of the absorbing layer 3 is available for the optical evaluation which, as stated above, results in an improvement of the exactitude of the measurement.

In the illustrated embodiment, the first carrier layer carrying the absorbing layer 3 is a comparatively stiff base film with a thickness of about 200 to 600 $\mu$m and the second carrying layer carrying the reagent layer 11 is a comparatively flexible covering film with a thickness of about 100 to 250 $\mu$m. This arrangement is especially preferred for the purposes of the present invention because the flexible covering film can be pressed well and smoothly on to the absorbing layer 3.

Furthermore, in the illustrated embodiment, the covering film 10 is transparent and the base film 2 opaque. This is necessary when, as in the case of the illustrated embodiment, measurement is to be made from the covering film side, which is especially preferred when the measurement system simultaneously serves for the pressing on of the flap 8.

However, within the scope of the present invention, other constructions are possible. Thus, for example, the base film 2 can be transparent and the covering film 10 can be pigmented in which case measurement is made from the base film side, i.e. from below in the case of FIG. 1.

For the exactitude of the analyses carried out with a test carrier according to the present invention, it is important that the reagent layer dissolves sufficiently quickly and completely so that the reagents penetrate in a short time uniformly into the liquid-absorbing layer and the optical measurement is not substantially disturbed by residues of the reagent layer. In order to select a suitable material from a large number of materials which appear to be suitable for making the reagent layer, the following selecting process can be used:

Aqueous solutions are prepared of the substance to be tested in such concentrations that readily coatable viscosities of about 30 to 50 mPa sec. result. To 100 ml. amounts of the solutions are added 100 mg. Tween 20 (a wetting agent which is commercially available from E. Merck, Darmstadt, Federal Republic of Germany) and 60 mg. of the dyestuff Patenblau V (also available from E. Merck). The solutions are coated in a wet film thickness of 0.1 mm, on to a polycarbonate film of 0.2 mm. thickness and dried at 60° C.

The suitability of a film layer so produced for the purpose of the present invention can be tested by dropping on 30 μl. of serum. In the case of an especially well suited film layer, especially when using xanthan as the film former, the droplet spreads out quickly. The dyestuff dissolves immediately and uniformly.

When using other less suitable substances as film formers, the droplet spreads out less quickly, i.e. initially the liquid remains standing in the form of a hemisphere. The dyestuff only dissolves slowly and optically recognisable streaks remain. With such a substance of film-forming material, a still useful result is admittedly achieved but high demands for measurement exactitude are not fulfilled.

To this group, which are admittedly suitable for the invention but less preferred, belong, apart from xanthan, the substances set out in the following Table 1. For each substance, there is given, in weight percent, the content in the solution which is necessary in order to adjust the viscosity, also given, from which, for example, a reagent layer according to the present invention can be produced.

TABLE 1

| substance | content in the coating solution (in wt. %) | viscosity (mPa sec.) |
|---|---|---|
| 1. polyvinylpyrrolidone (Kollidon K 17) | 30 | 30 |
| 2. polyvinyl alcohol (Moviol 18-88) | 4.5 | 35 |
| 3. polyvinyl alcohol (Moviol 26-88) | 4 | 35 |
| 4. methylcellulose (Tylose 6000) | 0.5 | 40 |
| 5. methylcellulose (Tylose 30000) | 0.5 | 45 |
| 6. methylhydroxyethylcellulose (Tylose MH 2000X P) | 1 | 45 |
| 7. hydroxyethylcellulose (Natrosol 250 G) | 2 | 40 |
| 8. sodium alginate (Kelcoalginate) | 0.6 | 40 |
| 9. xanthan gum (Keltrol) | 0.7 | 40 |

The substances are obtainable from the following manufacturers:
No. 1: BASF AG., Federal Republic of Germany
Nos. 2-6: Hoechst AG, Federal Republic of Germany
No. 7: Hercules, Federal Republic of Germany
Nos. 8 and 9: Kelco Division of Merck & Co., U.S.A.

The following Examples are given for the purpose of illustrating the present invention:

EXAMPLE 1

TEST CARRIER ACCORDING TO FIG. 1 FOR THE DETERMINATION OF AMYLASE IN BLOOD (a) Production of the reagent layer 11.

From 5 g. xanthan gum (Keltrol F) in the form of a 0.3% solution in 0.1M phosphate buffer (pH 7), 1000 U α-glucosidase (manufacturer: Boehringer Mannheim GmbH, Federal Republic of Germany), 50 mg. Tween 20 (wetting agent) and 150 g. indolyl-α-maltoheptaoside (colour-forming substrate), there is produced a coating mass which is coated with a wet film thickness of 0.1 mm. on to a transparent polycarbonate film with a thickness of 0.1 mm. (as covering film 10) and dried for 15 minutes at 50° C.

An alternative reagent film of otherwise identical composition is obtained when a 0.2% solution of Tylose 6000 in water is used instead of the xanthan gum solution.

(b) Production of the reagent carrier 9.

A solution of 60 mg. 4-(N-morpholino)-2-methoxyphenyldiazonium salt (colour strengthener) and 0.5 g. phosphoric acid trimorpholide (stabilizer) in 10 ml. water is used to impregnate a monofilar polyamide fabric Nylon 20 HC (producer: Schweizer Seidengase Fabrik, Thal, Switzerland), followed by drying for 10 minutes at 30° C.

The pre-reagent layer 6 is not present in this test.

(c) Measurement results.

The evaluation of the colour formation was carried out with the use of a "Reflotron" apparatus (manufacturer: Boehringer Mannheim GmbH, Federal Republic of Germany). Amylase-containing human serum was used as sample. Evaluation took place via empirically determined function curves in U/liter (units per liter). The measurement results obtained are set out in the following Table 2:

TABLE 2

| | per 15 measurement values with tylose-containing film | | per 15 measurement values with xanthan-containing film | |
|---|---|---|---|---|
| actual value (U/l.) | average value (U/l.) | variation coefficient VC (%) | average value (U/l.) | variation coefficient VC (%) |
| 152 | 149 | 10.4 | 154 | 4.08 |
| 290 | 281 | 5.8 | 293 | 2.48 |
| 741 | 732 | 7.4 | 746 | 1.39 |
| 1250 | 1177 | 5.9 | 1279 | 2.35 |

It can be seen that the measurement results obtained with the xanthan-containing film are clearly better. They all satisfy very high requirements in clinical chemistry. On the other hand, the measurement results with the tylose-containing film do not satisfy quite such high claims of exactitude. However, depending upon the purpose of use, for example a semiquantitative determination, the exactitude achieved with this film can also be sufficient.

In addition to the reflection-photometric measurement, after the measurement the test carriers were also assessed visually. It was thereby found that the absorbing layer recognisable under the covering film 10 was, in the case of the xanthan film, uniformly blue coloured, whereas the tylose-containing film showed a slight streak formation with localised faulty colouring. Upon removing the flap with forceps, in the case of the xanthan layer no undissolved residues could be seen under the flap. The tylose layer was admittedly also substantially dissolved but small residues clearly remained behind which could be seen by a streakiness.

EXAMPLE 2

TEST CARRIER ACCORDING TO FIG. 1 FOR THE DETERMINATION OF THE LOW CONCENTRATION PARAMETER BILIRUBIN IN BLOOD

Comparison between a test carrier according to the present invention and test carrier according to the prior art.

(a) Production of a reagent film according to the prior art (instead of reagent layer 11).

From 0.4 g. citric acid, 10 g. of a 50% polyvinyl propionate dispersion (Propionfan; BASF AG, Federal Republic of Germany), 15 g. of 1% hydroxyethylcellulose solution (thickener; Natrosol 250 G, Hercules), 0.3 g. Triton X 100 (wetting agent; E. Merck, Darmstadt, Federal Republic of Germany), 9.5 g. kieselguhr, 150 mg. 2,5-dichlorophenyldiazonium tetrafluoroborate (colour former) and 12 ml. water there is prepared a coating mass which is applied at a wet film thickness of 0.13 mm. to a transparent polycarbonate film with a thickness of 0.2 mm. and dried at 50° C. for 15 minutes.

(b) Production of the reagent film 11 according to the present invention.

From 10 mmole/l. 2,5-dichlorphenyldiazonium tetrafluoroborate in 0.6% xanthan gum in water there is produced a coating mass which is coated with a wet film thickness of 0.1 mm. on to a transparent polycarbonate film with a thickness of 0.1 mm. (as covering film 10) and dried for 15 minutes at 50° C.

(c) Production of the reagent layer 6 (pre-reagent for the liberation of conjugated bilirubin).

500 mmole/l. dyphylline in water are used to impregnate a long-fibre paper, followed by drying at 50° C. for 10 minutes.

The results of measurements made with a Reflotron apparatus with bilirubin-containing sera after a reaction time of 1 minute are set out in the following Table 3:

TABLE 3

| content (mg./dl.) | % remission kieselguhr film (a) | % remission test carrier of the present invention (b) |
|---|---|---|
| 1 | 60 | 62.5 |
| 2 | 58.5 | 58 |
| 4 | 56 | 52 |
| 8 | 52 | 44.5 |
| 12 | 48.5 | 39.5 |
| 20 | 45.5 | 32.5 |

It can be seen that the sensitivity in the case of the test carrier according to the present invention is about twice as high as in the case of the use of a reagent film according to the prior art. Having regard to the exactitude of measurement of the evaluation apparatus, there is thus achieved a substantial improvement of the exactitude of the analysis. This advantage manifests itself especially strongly particularly in low remission ranges, in which the present invention results in a very considerable improvement, because, in this range, a slight change of the remission corresponds, in the usual tests, to a comparatively strong change of the corresponding concentration.

In this Example, too, the layers used are additionally assessed visually. The kieselguhr film according to the prior art shows as indefinite distribution of the reaction colour. If the measurement area is examined from above, as by the measurement eye of the remission photometer, through the covering film 10 of the flap 8, only a pale coloration can be seen which is obviously only a fraction of the total reaction colour actually present. In contradistinction thereto, in the case of the film according to the present invention, a uniform, dark coloration is to be seen.

While there have been described what are at present considered to be the preferred embodiments of this invention, it will be obvious to one skilled in the art that various changes and modifications may be made therein without departing from the invention, and it is, therefore, aimed to cover all such changes and modifications as fall within the true spirit and scope of the invention.

We claim:

1. A device for analytical determination of a component in a liquid sample, comprising a first carrier layer having applied thereto a liquid absorbing layer, and a separate second movable carrier having applied thereto a dissolvable reagent-containing layer which is not in initial contact with said first carrier layer, said first carrier layer attached at a point to said second layer as a flap, wherein at least one of said first carrier layer and said second carrier layer is transparent, said liquid absorbing layer not in initial contact with said second carrier layer and said liquid absorbing layer comprising material which absorbs said reagent-containing layer when said reagent-containing layer is dissolved by contact with a liquid contained in said liquid absorbing layer, said first carrier layer being positioned in said device to permit contact between said liquid absorbing layer and said reagent-containing layer by applying pressure to one of said carrier layers.

2. Device of claim 1, wherein said reagent-containing layer has a thickness one half or less that of said liquid absorbing layer.

3. Device of claim 1, wherein said reagent-containing layer contains a binding agent, a swelling agent, or a thickening agent.

4. Device of claim 1, wherein said liquid absorbing layer is permeable to light and one of said carrier layers comprises material which diffusely reflects said light.

5. Device of claim 1, wherein said liquid-absorbing layer has a greater planar extension than said reagent containing layer.

6. Device of claim 1, wherein said liquid absorbing layer comprises material which transports liquid along its planar extension via capillarity.

7. Device of claim 1, wherein at least one of said carrier layers is a stiff film.

8. Device of claim 1, wherein at least one of said carrier layers is a flexible film.

9. Device of claim 1, wherein the reagent of said reagent-containing layer comprises an enzyme.

10. Device of claim 1, wherein said reagent-containing layer carries a chromogenic substance.

11. Device of claim 1, wherein said second carrier layer and said reagent-containing layer are connected to said first carrier layer at one end by a connecting means to permit pressing together of said first and second carrier layers.

12. Device of claim 1, wherein one of said carrier layers is a stiff film and the second of said carrier layers is a flexible film.

13. Device of claim 12, wherein said stiff film is from about 200 µm to about 600 µm thick and said flexible film is from about 100 µm to about 250 µm thick.

14. Device of claim 1, wherein said reagent-containing layer comprises a high molecular weight film which is soluble in water.

15. Device of claim 14, wherein said film comprises a polysaccharide.

16. Device of claim 14, wherein said film comprises xanthan.

17. Device of claim 1 further comprising a third carrier layer containing a reagent where the third layer is attached at the point between said first carrier layer and said second carrier layer whereby the reagent layers are separated until pressed together.

18. Device of claim 17, wherein said third layer comprises an open mesh material.

19. Device of claim 17, wherein said third layer comprises a fabric material.

* * * * *